United States Patent
Hogendijk et al.

(10) Patent No.: US 6,695,787 B2
(45) Date of Patent: Feb. 24, 2004

(54) PROSTATE VISUALIZATION DEVICE AND METHODS OF USE

(75) Inventors: Michael Hogendijk, Palo Alto, CA (US); Thomas C. Green, S.W. Seattle, WA (US); Isidro M. Gandionco, Fremont, CA (US); Ryan P. Boucher, San Francisco, CA (US); Yuri Belman, Sunnyvale, CA (US)

(73) Assignee: Neoseed Technology LLC., San Francisco, CA (US)

( * ) Notice: Subject to any disclaimer, the term of this patent is extended or adjusted under 35 U.S.C. 154(b) by 0 days.

(21) Appl. No.: 10/160,341

(22) Filed: May 31, 2002

(65) Prior Publication Data

US 2003/0050526 A1 Mar. 13, 2003

Related U.S. Application Data

(63) Continuation-in-part of application No. 09/648,319, filed on Aug. 25, 2000, now Pat. No. 6,422,997.
(60) Provisional application No. 60/295,408, filed on May 31, 2001.

(51) Int. Cl.[7] .................................................. A61B 8/14
(52) U.S. Cl. ...................................................... 600/463
(58) Field of Search ................................ 600/439, 462, 600/463, 204, 207, 159, 3, 437, 459–461, 466; 606/191, 192, 198; 320/128; 604/101.05, 104, 8, 101.03, 49, 96, 508, 509

(56) References Cited

U.S. PATENT DOCUMENTS

| | | | |
|---|---|---|---|
| 4,700,692 A | | 10/1987 | Baumgartner |
| 4,973,301 A | * | 11/1990 | Nissenkorn ..................... 604/8 |
| 5,085,664 A | * | 2/1992 | Bozzo ......................... 606/191 |
| 5,098,374 A | * | 3/1992 | Othel-Jacobsen et al. ...... 604/8 |
| 5,188,596 A | | 2/1993 | Condon et al. |
| 5,209,725 A | | 5/1993 | Roth |
| 5,301,688 A | | 4/1994 | Stepjen et al. |
| 5,358,496 A | * | 10/1994 | Ortiz et al. .................. 606/198 |
| 5,409,483 A | | 4/1995 | Campbell et al. |
| 5,449,994 A | * | 9/1995 | Armand et al. ............. 320/128 |
| 5,458,612 A | | 10/1995 | Chin |

(List continued on next page.)

*Primary Examiner*—Max F. Hindenburg
*Assistant Examiner*—Nikita R Veniaminov
(74) *Attorney, Agent, or Firm*—Fish & Neave; Daniel M. Becker; Douglas A. Oguss

(57) ABSTRACT

Methods and apparatus are provided for improved administration of brachytherapy in the treatment of prostate disease. More particularly, a prostate visualization device is provided comprising a catheter coupled to at least one deployable member at the distal end of the catheter. The deployable member is preferably manufactured from a shape memory alloy having a petal-shaped configuration suitable for engaging and defining the proximal region of a patient's bladder. The deployable member may comprise tubing filled with air or other radiopaque agents to facilitate ultrasonic imaging of the deployable members near the bladder/prostate junction.

73 Claims, 8 Drawing Sheets

U.S. PATENT DOCUMENTS

| | | | |
|---|---|---|---|
| 5,492,529 A | | 2/1996 | Neuwirth et al. |
| 5,588,965 A | * | 12/1996 | Burton et al. ........... 604/101.05 |
| 5,626,829 A | | 5/1997 | Koutrouvelis |
| 5,628,746 A | | 5/1997 | Clayman |
| 5,628,770 A | | 5/1997 | Thome et al. |
| 5,645,528 A | | 7/1997 | Thome |
| 5,715,825 A | | 2/1998 | Crowley |
| 5,848,969 A | * | 12/1998 | Panescu et al. .............. 600/462 |
| 5,855,563 A | | 1/1999 | Kaplan et al. |
| 5,865,728 A | * | 2/1999 | Moll et al. ................... 600/204 |
| 5,868,778 A | | 2/1999 | Gershony et al. |
| 5,871,448 A | | 2/1999 | Ellard |
| 5,876,417 A | * | 3/1999 | Devonec et al. ............ 606/192 |
| 5,899,882 A | | 5/1999 | Waksman et al. |
| 5,916,153 A | | 6/1999 | Rhea, Jr. |
| 5,928,130 A | | 7/1999 | Schmidt |
| 5,938,583 A | | 8/1999 | Grimm |
| 5,993,447 A | | 11/1999 | Blewett et al. |
| 6,033,413 A | | 3/2000 | Mikus et al. |
| 6,036,631 A | | 3/2000 | McGrath et al. |
| 6,059,812 A | | 5/2000 | Clerc et al. |
| 6,071,263 A | * | 6/2000 | Kirkman ...................... 604/104 |
| 6,083,166 A | | 7/2000 | Holdaway et al. |
| 6,106,521 A | | 8/2000 | Blewett et al. |
| 6,213,976 B1 | | 4/2001 | Trerotola |
| 6,221,006 B1 | * | 4/2001 | Dubrul et al. ............... 600/159 |
| 6,299,598 B1 | | 10/2001 | Bander |
| 6,366,818 B1 | | 4/2002 | Bolmsjo |
| 6,413,204 B1 | | 7/2002 | Winkler et al. |
| 6,422,997 B1 | | 7/2002 | Green et al. |
| 6,447,505 B2 | | 9/2002 | McGovern et al. |
| 6,482,178 B1 | | 11/2002 | Andrews et al. |

* cited by examiner

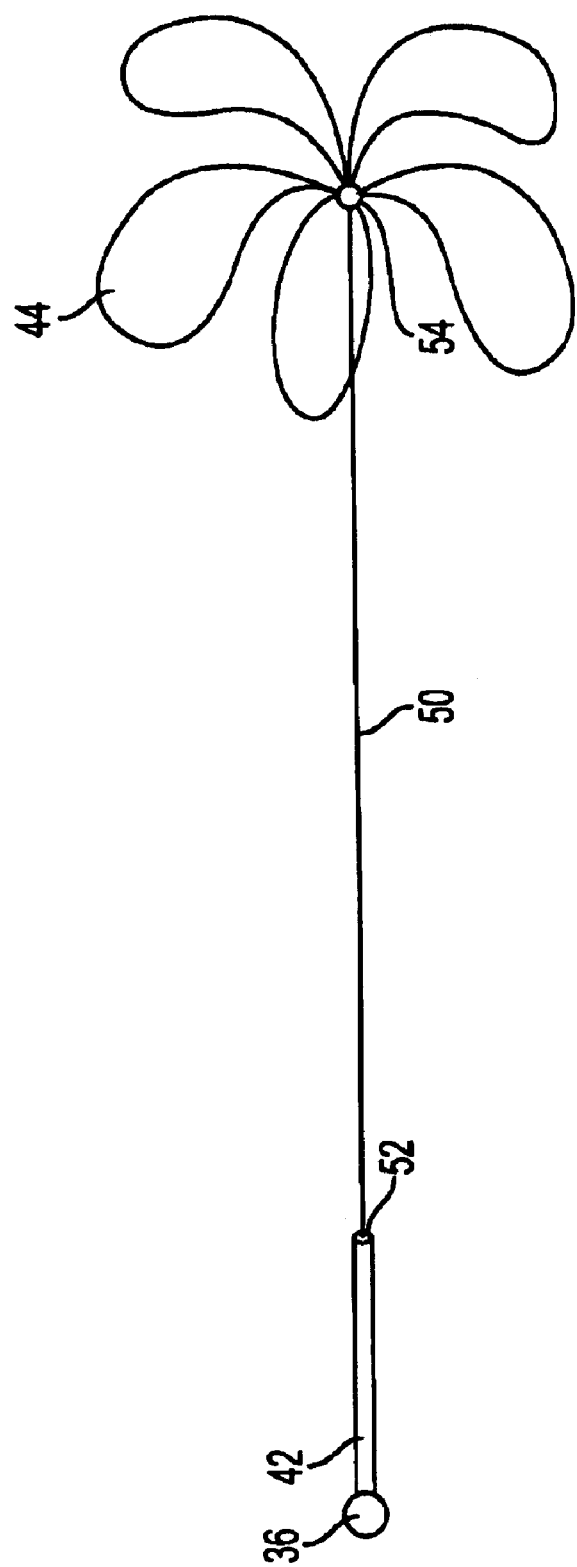

PROSTATE VISUALIZATION DEVICE AND METHODS OF USE

REFERENCE TO RELATED APPLICATION

The present application is a continuation-in-part of U.S. patent application Ser. No. 09/648,319, filed Aug. 25, 2000, now is U.S. Pat. No. 6,422,997 and claims the benefit of the filing date of U.S. provisional application Ser. No. 60/295,408, filed May 31, 2001, the disclosure of which is incorporated herein by reference in its entirety.

FIELD OF THE INVENTION

This invention relates to improved apparatus and methods for the treatment of prostate cancer. More particularly, the present invention provides a prostate visualization device having at least one deployable member suitable for imaging the bladder/prostate junction, and methods of use.

BACKGROUND OF THE INVENTION

Excluding nonmelanoma skin cancers, prostate cancer is the most common cancer afflicting American men. The American Cancer Society estimates that over 180,000 new cases will be diagnosed in the U.S. in the year 2000 alone, and that nearly 32,000 people will die from the disease. Prostate cancer is second only to lung cancer as the leading cause of cancer death in men, accounting for roughly 11%.

Prostate cancer is defined as malignant tumor growth within the prostate gland. Its cause is unknown, although high dietary fat intake and increased testosterone levels are believed to be contributory factors. A letter scale ("A" through "D"), which accounts for the location of the cancer, is commonly used to classify the stage of disease. In Stage A, the tumor is not palpable but is detectable in microscopic biopsy. Stage B is characterized by a palpable tumor confined to the prostate. By Stage C, the tumor extends locally beyond the prostate with no distant metastasis. By Stage D, cancer has spread to the regional lymph nodes or has produced distant metastasis.

In the early stages, prostate cancer is most commonly treated by either prostate removal or by brachytherapy. More advanced cases are treated by hormonal manipulation or orchiectomy to reduce testosterone levels and curb spreading of the disease, by chemotherapy, or by external beam radiation therapy.

With regard to treatment of early stage prostate cancer, the state of the art has several drawbacks. Radical prostatectomy is often recommended for treatment of localized stage A and B prostate cancers. Under general or spinal anesthesia, an incision is made through a patient's abdomen or perineal area, and the diseased prostate is removed. The procedure is lengthy, especially if a lymph node dissection is simultaneously performed, and requires a hospital stay of 2–5 days. Possible complications include impotence and urinary incontinence.

Internal radiation therapy or brachytherapy has recently been developed and holds great promise for the treatment of early stage prostate cancer. Radioactive pellets or seeds of, for example, iodine-125, palladium-103, or iridium-192, are deposited directly into the prostate through needle placement. U.S. Pat. No. 5,928,130 to Schmidt provides a slightly modified example of such a needle device. Imaging techniques, such as transrectal ultrasound, CT scans, or MRI, are used to accurately guide placement of the radioactive material. Advantageously, radiation from the brachytherapy seeds is administered directly to the prostate with less damage to surrounding tissues, delivering a substantially higher radiation dosage to the prostate than to the surrounding tissues, as compared to external beam radiation therapy. The procedure need only be performed once, and impotence and urinary incontinence complications are significantly reduced, as compared to prostate removal procedures.

The seeds, which are permanently implanted, give off radiation for weeks or months. Their presence causes little discomfort, and they remain in the prostate after decay of the radioactivity. For several weeks following needle insertion, patients may experience pain in the perineal area, and urine may have a red-brown discoloration.

Although, when performed correctly, brachytherapy may provide several benefits when compared to prostate removal and other techniques, current apparatus and methods for delivering the seeds to target locations within the prostate are somewhat crude and are subject to practitioner error. The current method of identifying the depth of needle insertion is by ultrasound imaging. The junction of the base of the prostate and the bladder provides a common reference plane for needle insertion. Identifying this critical reference "base" plane is critical to proper needle and seed placement.

One previously known technique for imaging the base plane is to visualize the plane in either transverse or sagittal ultrasound imaging. Injection of contrast agent may facilitate imaging. A catheter, such as a standard Foley catheter, may be inserted into the patient's urethra proximal of the junction. Contrast agent comprising aerated K-Y jelly and water, may then be injected through an end port of the catheter. The agent moves distally towards the patient's bladder and is visible to an ultrasound probe, positioned in the patient's rectum, thereby facilitating imaging.

Attempts have been made to improve Foley catheters, as well as to facilitate improved imaging within a body lumen. For example, U.S. Pat. No. 5,715,825 to Crowley provides an acoustic imaging catheter with an inflatable dilation balloon and an ultrasound transducer. However, while Crowley may provide improved imaging, the device is mechanically and electrically complex, and is therefore costly. U.S. Pat. No. 5,916,153 to Rhea, Jr. provides a multifunction, modified Foley catheter. The device described in that patent, however, does not improve on current junction imaging techniques.

In view of the drawbacks associated with previously-known methods and apparatus for bladder/prostate junction imaging, it would be desirable to provide methods and apparatus that overcome such drawbacks.

It further would be desirable to provide methods and apparatus that provide reliable imaging of the bladder/prostate junction.

It still further would be desirable to provide methods and apparatus that may be used in conjunction with standard brachytherapy apparatus.

SUMMARY OF THE INVENTION

In view of the foregoing, it is an object of the present invention to provide methods and apparatus for bladder/prostate junction imaging that overcome drawbacks associated with previously-known methods and apparatus.

It is also an object of the present invention to provide methods and apparatus that provide reliable imaging of the bladder/prostate junction.

It still further is an object to provide methods and apparatus that may be used in conjunction with standard brachytherapy apparatus.

These and other objects of the present invention are accomplished by providing methods and apparatus for bladder/prostate junction imaging comprising a catheter having at least one distally deployable member that engages and defines the proximal region of the bladder. The deployable member is preferably constructed from a shape memory material that forms a petal-shaped configuration upon deployment. The deployable member is deployed within the patient's bladder, and may be retracted proximally to conform to the proximal wall of a patient's bladder. Gas pockets may be provided around the deployable member to enhance visibility with an ultrasound probe. Additionally, echo-contrast agent may be injected to the region to facilitate reliable imaging.

In a preferred embodiment, the deployable member comprises a plurality of petal-shaped Nitinol wires affixed to the distal end of a plunger that is coupled to a multi-lumen catheter. The catheter may include a deployment lumen, a bladder drainage lumen, a contrast injection lumen, and a prostatic therapy lumen. The catheter is advanced through a patient's urethra into the patient's bladder. The deployable member is deployed by advancing the plunger distally within the deployment lumen. Upon deployment within the bladder, the plunger is proximally retracted until the deployable member engages the proximal wall of the bladder. Echo-contrast agent then may be injected into a space near the bladder/prostate junction. Ultrasonic imaging may then proceed, often with an ultrasound probe positioned in the patient's rectum. Urine also may be emptied from the bladder via the bladder drainage lumen, and the patient's prostate may be accessed via the prostatic therapy lumen.

The deployment lumen may be used in combination with any of the drainage, contrast, and prostatic therapy lumens. In alternative embodiments, one or more catheter lumens may be configured to serve more than one function. For example, a single lumen catheter having only one distal outlet port may be provided whereby one or more proximal ports are in communication with the outlet port via the single lumen. In this embodiment, the single lumen of the catheter allows for passage of the deployable member, fluid injection, fluid drainage and delivery of prostatic therapy devices or therapeutic agents.

Additionally, tubing may cover the deployable member to form gas pockets around the deployable member such that the gas enhances ultrasonic imaging of the bladder/prostate junction. The tubing may comprise a variety of shapes and sizes to facilitate imaging of the deployable member.

Methods of using the present invention are also provided.

BRIEF DESCRIPTION OF THE DRAWINGS

Additional objects and advantages of the invention will be apparent from the following description, the appended claims, and the accompanying drawings, in which like reference characters refer to like parts throughout, and in which:

FIG. 5 illustrates an actuation mechanism for the deployable member;

DETAILED DESCRIPTION OF THE INVENTION

The present invention provides methods and apparatus for improved administration of brachytherapy. More particularly, the present invention provides a prostate visualization device comprising at least one distally deployable member that engages and defines the proximal wall of a patient's bladder. The device is preferably coupled to a catheter to facilitate imaging of the patient's bladder/prostate junction.

Figure 1:
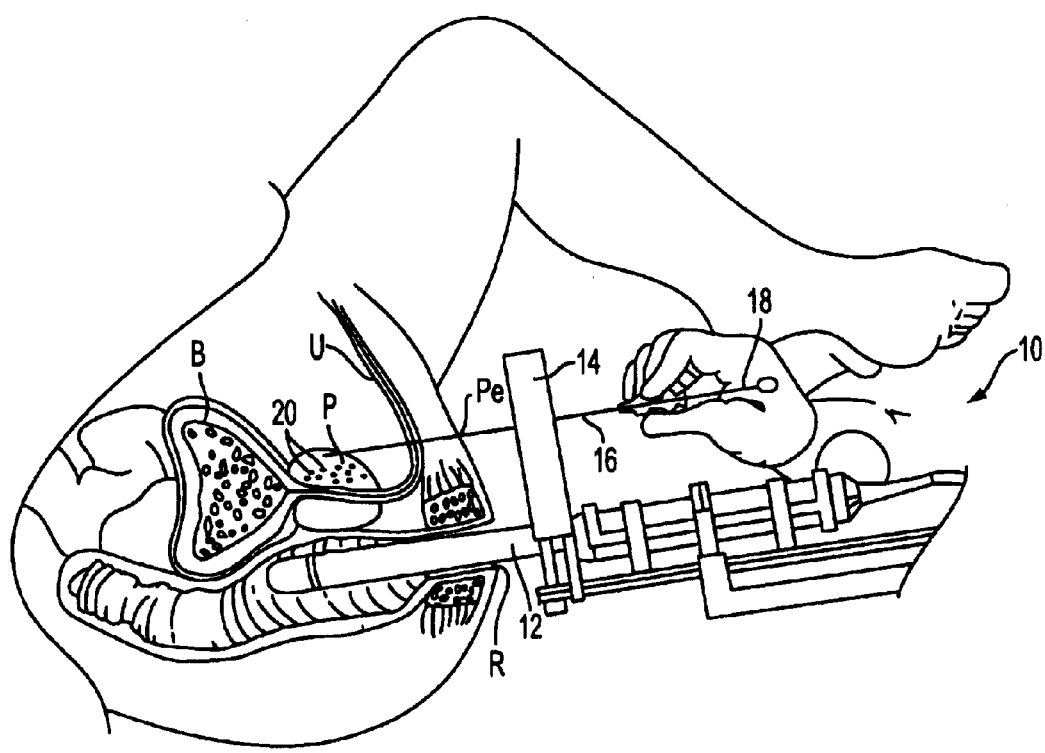
FIG. 1 is a schematic view of a prior art method of performing brachytherapy.
Figure 2:
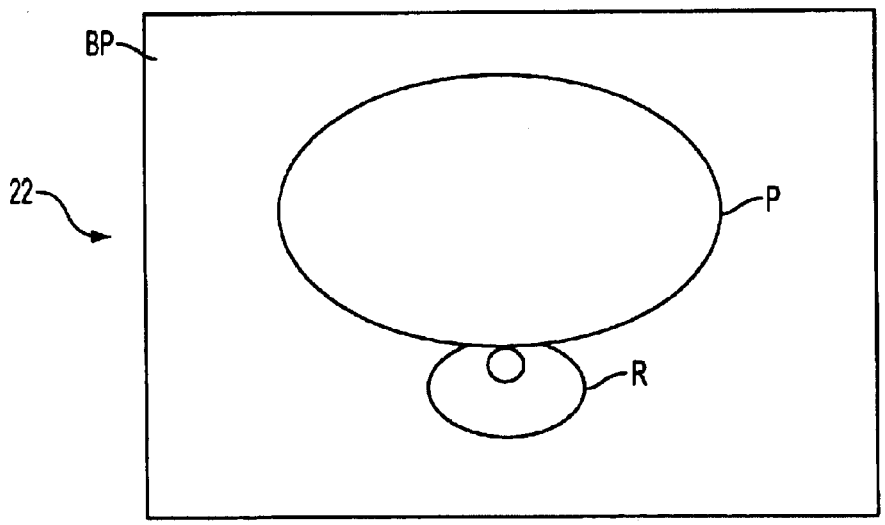
FIG. 2 is a schematic view detailing the prior art method of imaging the bladder/prostate junction in greater detail.

Referring to FIGS. 1 and 2, a prior art method of performing brachytherapy is described. The method and apparatus are as taught by Peter Grimm, DO, in a pamphlet entitled, "Ultrasound Guided Implantation of the Prostate: A Practical Review Course." As seen in FIG. 1, brachytherapy apparatus 10 comprises transrectal ultrasound probe 12, guide block 14, needle 16, plunger 18, and radioactive seeds 20. Ultrasound probe 12 is advanced through a patient's rectum R to facilitate imaging of the patient's prostate P. Prostate P surrounds urethra U and is just proximal of bladder B. An ultrasonic image of a junction between the prostate and the bladder is acquired, as described hereinbelow with respect to FIG. 2. Needle 16, loaded with seeds 20 and plunger 18, is then advanced through guide block 14, through the patient's perineum Pe, and into prostate P, where needle 16 is retracted while plunger 18 is held stationary to sew the seeds in a line within prostate P.

With reference to FIG. 2, the imaging aspect of the apparatus and method of FIG. 1 is described in greater detail. A catheter, such as a standard Foley catheter, is inserted into the patient's urethra proximal of the patient's bladder/prostate junction. A combination of water and KY jelly is then injected through an end port of the catheter. The combination moves distally towards the patient's bladder and appears to ultrasound probe 12 as contrast agent. Ultrasound probe 12 then provides signals that are converted by a previously known ultrasound system to display ultrasonic image 22 of base plane BP, which is located tangent to the distal surface of prostate P, i.e. at the prostate/bladder junction. All positions within the prostate are determined relative to base plane BP during the brachytherapy procedure.

Ultrasonic imaging and location determination of base plane BP may be unreliable due to irregular ultrasonic images dependent on a density of the water/KY jelly combination at a given location, as well as flow conditions within the bladder and urethra. Thus, there exists a need for reliable apparatus and methods for bladder/prostate junction imaging.

Figure 3A:
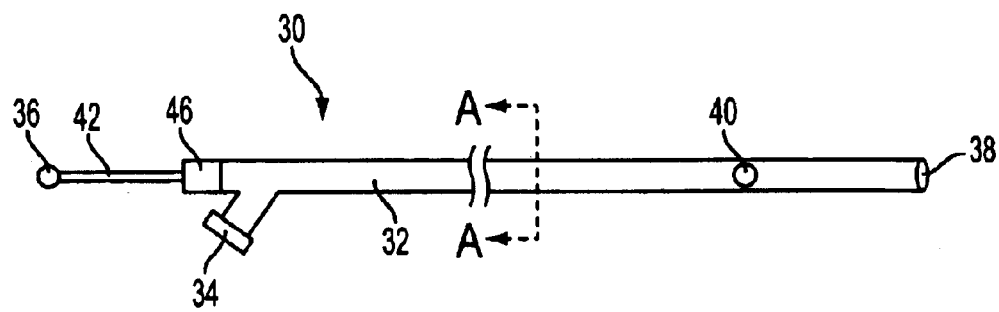
FIGS. 3A–3C are, respectively, a side view of apparatus constructed in accordance with the present invention in a collapsed delivery state, a sectional view of the apparatus through section line A—A of FIG. 3A, and a side view, partly in section, of the apparatus in an expanded deployed state.
Figure 3B:
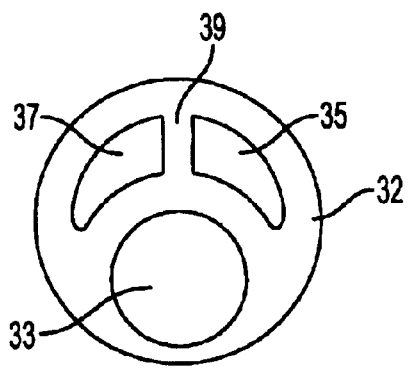
Figure 3C:
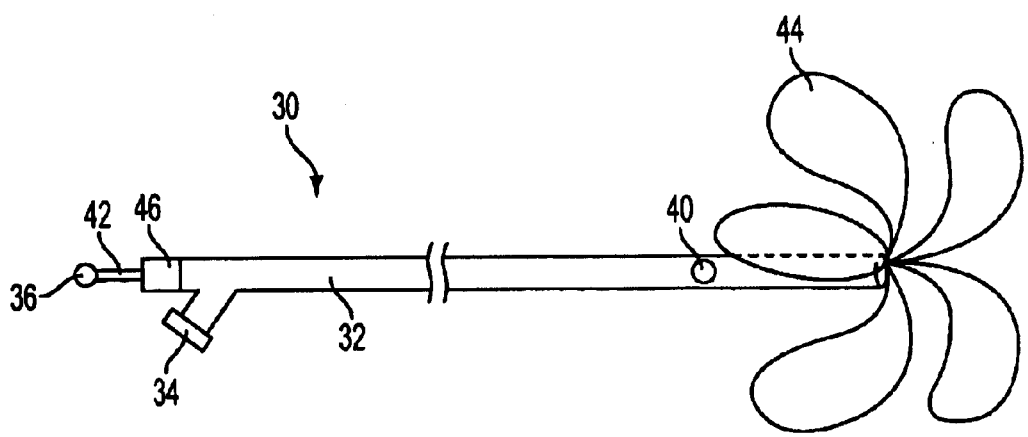

Referring now to FIG. 3, a first embodiment of apparatus constructed in accordance with the present invention is described. Apparatus 30 comprises catheter 32 and plunger 42 having handle 36. Plunger 42 may span the approximate length of catheter 32 such that it is directly affixed to deployable member 44 of FIG. 3C. Alternatively, plunger 42 may be affixed to the proximal end of a connector, and the distal end of the connector may be affixed to deployable member 44, as described in FIG. 5 hereinbelow.

Catheter 32 further comprises deployment lumen 33 and contrast lumen 35. A second contrast lumen 37 may be provided, and contrast lumens 35 and 37 may be separated by optional dividing wall 39 to enhance catheter stability during injection of the contrast agent.

Deployment lumen 33 extends between proximal deployment port 46 and distal deployment port 38. Proximal deployment port 46 is preferably a hemostatic port, e.g., a Touhy-Borst connector, that enables plunger 42 to slide longitudinally through the port while inhibiting fluid transfer. Contrast lumens 35 and 37 extend between proximal contrast port 34 and distal contrast port 40, which is located proximal of distal deployment port 38. Catheter 32, excluding plunger 42 and handle 36, preferably comprises a total length of 30–50 cm.

Deployable member 44 is expandable from a collapsed delivery configuration within deployment lumen 33, to an expanded deployed configuration, as shown in FIG. 3C. In the deployed configuration, deployable member 44 is suitable for engaging and defining the proximal wall of a patient's bladder. Deployment member 44 preferably is provided in a petal or hoop shape, and may comprise a shape memory material, e.g., a Nickel-Titanium alloy (commonly known in the art as Nitinol). The predetermined shape is set by constraining the Nitinol element on a mandrel or fixture of the desired shape, then applying an appropriate heat treatment.

Deployable member 44 preferably is provided in a concave configuration with respect to the bladder/prostate junction. The member is flexible such that it may automatically conform to the shape of the proximal wall of the bladder, without imposing excessive pressure on the prostate or bladder upon retraction of the member against the proximal wall of the bladder. In a preferred embodiment, deployable member 44 comprises twelve petal-shaped members, although greater or fewer numbers of petal-shaped members may be used. The petal-shaped members may either overlap circumferentially or be spaced apart circumferentially when deployed.

Figure 4:
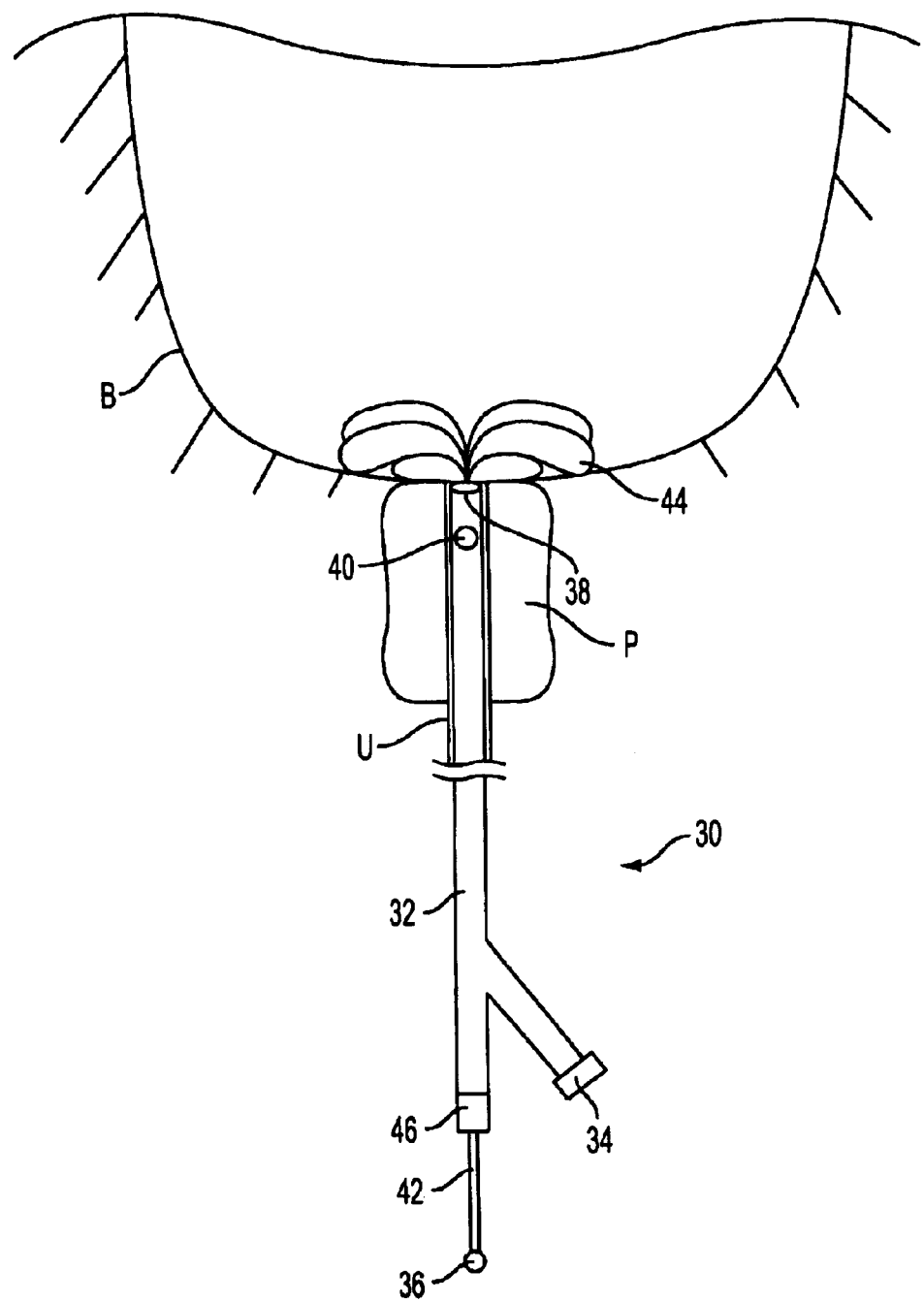
FIG. 4 is a schematic view, partly in cross-section, demonstrating a method of using the apparatus of FIG. 3 to image a patient's bladder/prostate junction.

Referring now to FIG. 4, a method of using apparatus 30 in accordance with the principles of the present invention is described. Catheter 32 is advanced through a patient's urethra U into bladder B, with deployable member 44 in a collapsed delivery configuration. Plunger 42 then is advanced distally, e.g., by pushing handle 36 of plunger 42 distally while retaining catheter 32 stationary, such that deployable member 44 extends beyond distal deployment port 38 of catheter 32. Deployable member 44 then self-expands to a predetermined, deployed configuration, as shown in FIG. 4.

Catheter 32 then is retracted out of bladder B to a desired position within urethra U. Alternatively, catheter 32 first may be placed at the desired position within the urethra and plunger 42 then is advanced distally to push deployable member 44 through the remaining portion of the urethra and into the bladder. With deployable member 44 in the expanded configuration, plunger 42 is retracted proximally until deployable member 44 engages a proximal region of bladder B.

Echo-contrast agent then may be injected through proximal contrast port 34 so that it exits distal contrast port 40. Contrast lumens 35 and 37, and ports 34 and 40, are preferably dimensioned in a manner that accounts for the viscosity of the agent. Once the contrast agent has been injected, apparatus 30 facilitates reliable ultrasonic imaging with ultrasound probe 12 inserted through the patient's rectum R, as shown in FIG. 1, and enables determination of a reliable reference plane, as depicted in FIG. 2. The reference plane may be used to conduct or to prepare for brachytherapy treatment of prostate cancer, in the manner discussed hereinabove.

With respect to FIG. 5, a mechanism for actuating the deployable member is described. Plunger 42 of FIG. 3 may be affixed to connector 50 via adhesive 52. Plunger 42 preferably comprises a relatively rigid material suitable for longitudinally sliding though proximal deployment port 46. Connector 50 preferably comprises a relatively elastic material that may adapt to the curvature of catheter 32, i.e., during transurethral insertion of catheter 32. Connector 50 may, for example, comprise a coil, a straight wire, a plastic rod, or any other configuration having elastic properties.

Connector 50 may be affixed to deployable member 44 via adhesive 54. Alternatively, connector 50 may be omitted and plunger 42 may span the approximate length of catheter 32 such that it is directly affixed to deployable member 44. In this embodiment, plunger 42 may comprise a relatively rigid proximal section and a more elastic distal section that spans the majority of the length of catheter 32.

Referring now to FIG. 6, alternative embodiments for enhancing ultrasonic imaging of the deployable member are described. In FIG. 6A, deployable member 81 is preferably constructed from shape memory wire 80 that expands to the deployed, petal-shape illustrated. Shape memory wire 80 may be covered with biocompatible tubing 82.

Biocompatible tubing 82 may be affixed to wire 80 by a biocompatible adhesive 84. The inner diameter of tubing 82 is sized to form gas pocket G around wire 80. Gas pocket G may comprise air, or any other radiopaque material, to enhance radiopaque imaging of deployable member 81 within the body.

Figure 6A:
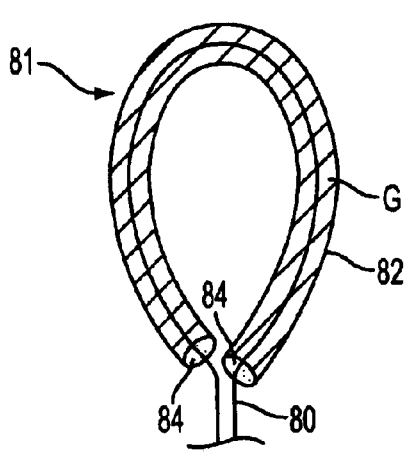
FIGS. 6 illustrate alternative embodiments for enhancing ultrasonic imaging of the deployable member.
Figure 6B:
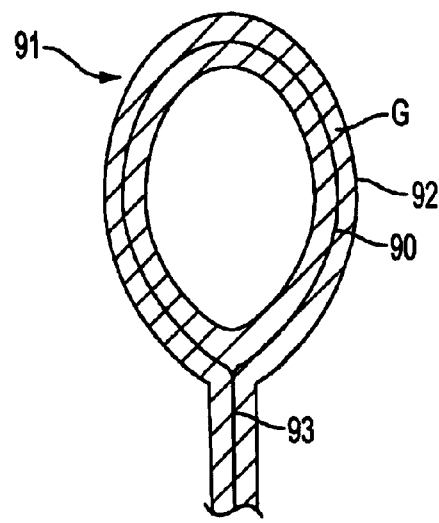

Alternatively, tubing 92 may completely surround deployable member 91 and may extend toward the proximal end of catheter 32, as shown in FIG. 6B. In this embodiment, tubing 92 surrounds wire 90 and plunger 93 such that gas pocket G is visible along the length of catheter 32. An optional inflation port (not shown) may be added to the apparatus of FIG. 3, and the inflation port may be coupled to the tubing such that additional gas G may be added to or removed from within the tubing.

Figure 6C:
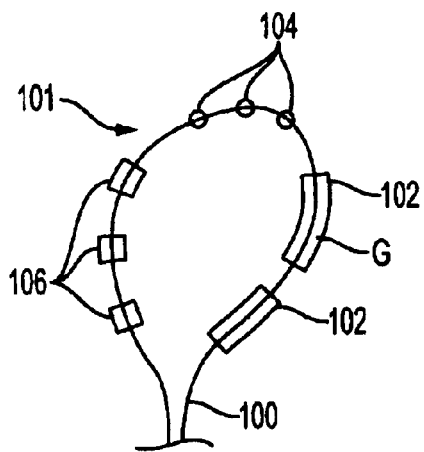

FIG. 6C illustrates deployable member 101 comprising various tubing configurations that are intermittently spaced around deployable member 101. Tubing pieces 102 are affixed at spaced increments around wire 100, each piece of tubing being suitable for housing gas pockets G to facilitate ultrasonic imaging of deployable member 101. Intermittently spacing the tubing around wire 100 may provide less resistance as wire 100 deploys to its predetermined configuration. Similarly, smaller tubing pieces 106 or rounded tubing pieces 104 may be intermittently spaced around deployable member 101.

Figure 6D:
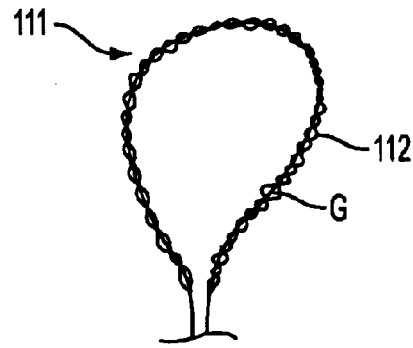

In FIG. 6D, deployable member 111 comprises plurality of interwoven wires 112. Plurality of interwoven wires 112 are loosely wrapped such that gaps exist between the wires. Advantageously, these gaps may trap gas bubbles G to facilitate ultrasonic imaging of deployable member 111 near the bladder/prostate junction.

Figure 6E:
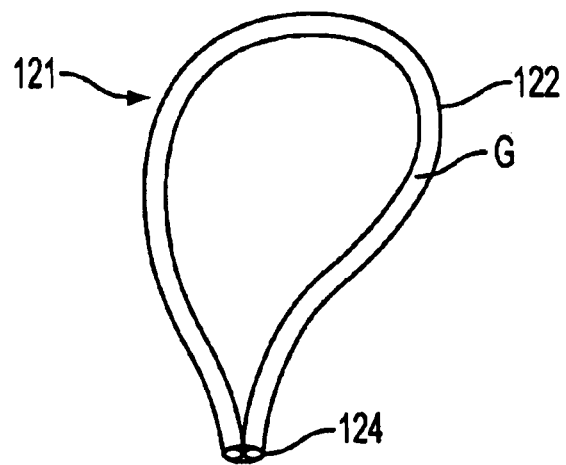

In FIG. 6E, deployable member 121 comprises a single piece of tubing 122 configured to deploy to a predetermined shape. In this embodiment, the proximal end of tubing 122 is sealed by plug 124 to confine contrast gas G. Alternatively, plug 124 may be omitted and tubing 122 may be coupled to a proximal inflation port (not shown) such that a radiopaque contrast agent may be injected into or removed from tubing 122.

Figure 7:
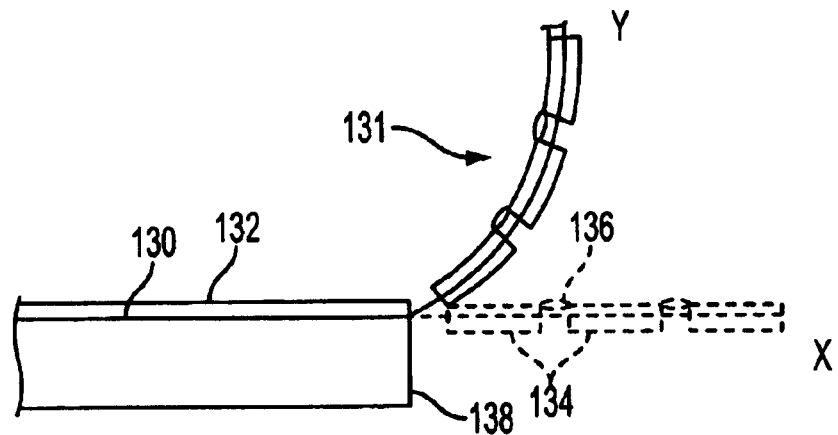
FIG. 7 illustrates an alternative mechanism for actuating the deployable member.

In FIG. 7, an alternative mode of actuating deployable member 131 is depicted. Deployable member 131 comprises wire 130 having hinging member 134. Hinging member 134 is initially constrained within catheter 132 during transurethral insertion of the device, as illustrated by the dotted line outline of position X. Upon positioning, wire 130 is advanced distally, e.g., by distally advancing plunger 42 of FIG. 1, such that hinging member 134 is advanced distal to port 138. Hinges 136 provide torsional rotation that allow hinging member 134 to expand to a curved configuration, as illustrated by position Y, suitable for conforming to the proximal wall of the patient's bladder.

Figure 8A:
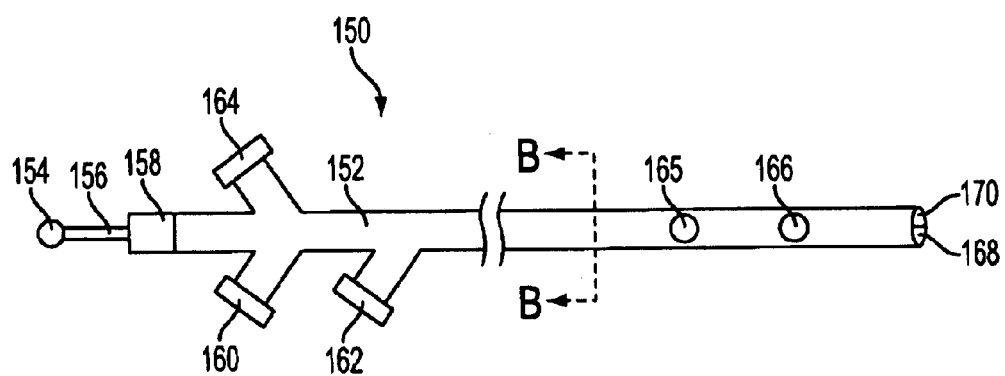
FIGS. 8A–8B are, respectively, a side view of an alternative apparatus constructed in accordance with the present invention in a collapsed delivery state, and a sectional view of the apparatus through section line B—B of FIG. 8A.
Figure 8B:
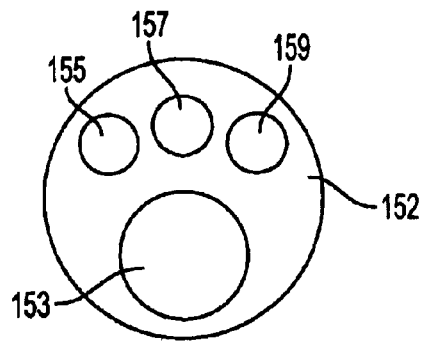

Referring now to FIG. 8, a further alternative embodiment of the catheter of the present invention is described. Catheter 152 comprises deployment lumen 153, prostatic therapy lumen 155, contrast lumen 157, and bladder drainage lumen 159. Deployment lumen 153 extends between proximal deployment port 158, e.g., a Touhy-Borst connector, and distal deployment port 170. Contrast lumen 157 extends between proximal contrast port 160 and distal contrast port 166, which is located proximal of distal deployment port 170. Prostatic therapy lumen 155 extends between proximal prostate port 164 and distal prostate port 165, which is located proximal of distal contrast port 166. Bladder drainage lumen 159 extends between proximal drainage port 162 and distal drainage port 168, which is located adjacent to distal deployment port 170.

Urine and other fluids may be emptied from the patient's bladder B of FIG. 8 during and after imaging via bladder drainage lumen 168. Urine enters distal drainage port 168, passes through drainage lumen 159 and exits the patient's body through proximal drainage port 162.

Prostatic therapy lumen 155 provides access to the patient's prostate P of FIG. 8. Therapeutic agents or interventional devices may be inserted into lumen 155 through proximal prostate port 164, and deposited into the patient's prostate P via distal prostate port 165. Apparatus 150 thus may be used for a variety of procedures which will be apparent to those of skill in the art and of which brachytherapy is only one example. Furthermore, it should be appreciated that deployment lumen 153 and its respective ports may be used in conjunction with any of the other three lumens described hereinabove, and their respective ports.

Figure 9A:
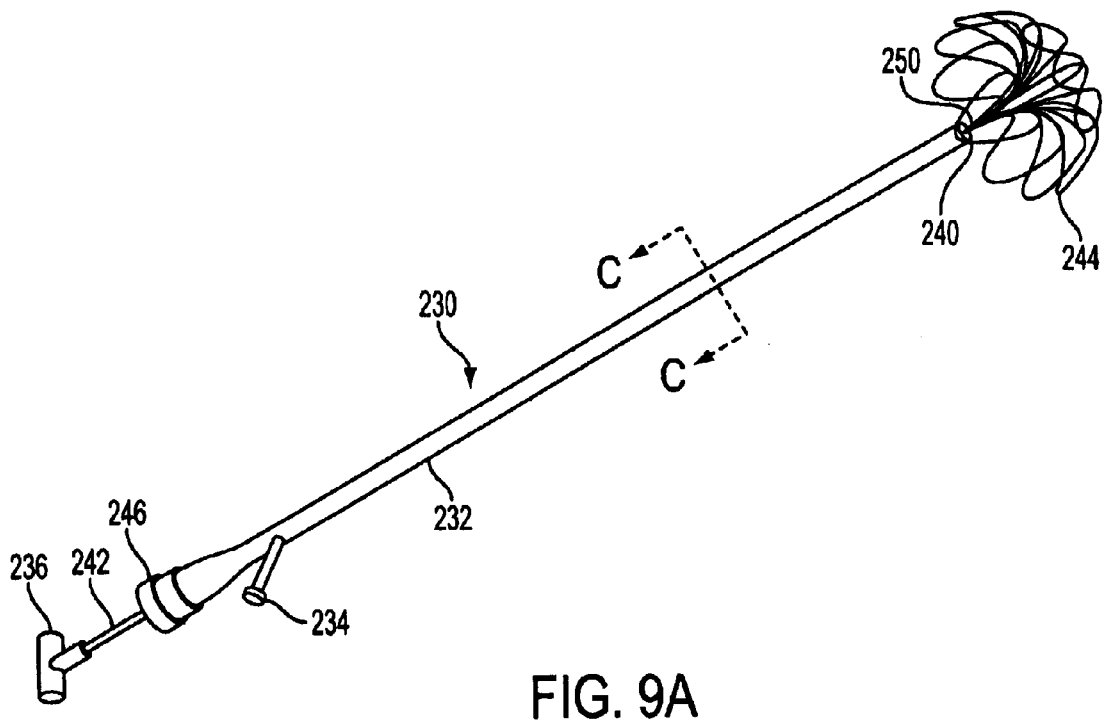
FIGS. 9A–9B are, respectively, a side view of a further alternative embodiment constructed in accordance with the present invention in a deployed state, and a cross-sectional view through line C—C of FIG. 9A.
Figure 9B:
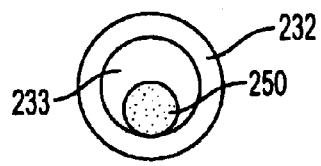

Referring now to FIGS. 9A–9B, a further alternative embodiment of a catheter of the present invention is described. In FIG. 9A, apparatus 230 comprises catheter 232 having plunger 242 disposed within lumen 233 thereof. Plunger 242 includes handle 236 and is coupled to deployable member 244, for example, via connecting rod 250, as described hereinabove with respect to FIG. 5. In this embodiment, catheter 232 comprises single lumen 233, as shown in FIG. 9B, that is configured to be used as a deployment lumen, contrast lumen, bladder drainage lumen and, optionally, as a prostatic therapy lumen. This configuration eliminates the need for two or more separate lumens, and reduces the overall profile of catheter 232.

In the embodiment of FIG. 9A, proximal deployment port 246 and proximal contrast port 234 preferably are similar to ports 46 and 34 of FIG. 3A, respectively, except that each of ports 246 and 234 communicate with lumen 233. Accordingly, contrast may be injected into proximal contrast port 234, flow through lumen 233 alongside connecting rod 250, and exit through distal outlet port 240, which forms as an opening at the distalmost end of catheter 232. In this embodiment, distal outlet port 240 also serves as the deployment port through which deployable member 244 is extended to self-deploy.

In the embodiment of FIG. 9, the wire loops forming the petal-shaped members at least partially overlap, thereby enhancing the structural rigidity of the petal-shaped members when deployed. As in the embodiment of FIG. 5, the petal-shaped members preferably comprise a shape-memory biocompatible alloy, such as nickel-titanium.

Although particular embodiments of the present invention have been described above in detail, it will be understood that this description is merely for purposes of illustration. Specific features of the invention are shown in some drawings and not in others; this is for convenience only, and any feature may be combined with another in accordance with the invention. Further variations will be apparent to one skilled in the art in light of this disclosure and are intended to fall within the scope of the appended claims.

What is claimed is:

1. Apparatus for facilitating visualization of a patient's prostate/bladder junction, comprising:

a catheter having proximal and distal ends, a proximal deployment port at the proximal end, a first outlet port at the distal end, and a first lumen extending therebetween;

a plunger having proximal and distal ends, the plunger configured to slide longitudinally through the proximal deployment port; and at least one deployable member coupled to the distal end of the plunger, wherein the deployable member is expandable from a delivery configuration adapted for transurethral insertion, to a deployed configuration adapted for engagement of a proximal portion of the patient's bladder, wherein the deployable member comprises at least one wire loop having a roughened exterior surface, the roughened exterior surface adapted to entrap gas bubbles to facilitate ultrasonic imaging.

2. The apparatus of claim 1 wherein the catheter further comprises a second inlet port, a second outlet port and a second lumen extending therebetween.

3. The apparatus of claim 2 wherein the catheter further comprises a third inlet port, a third outlet port and a third lumen extending therebetween.

4. The apparatus of claim 1 wherein the wire loop comprises a shape memory material.

5. The apparatus of claim 4 wherein the wire loop consists of a Nickel Titanium alloy.

6. The apparatus of claim 1 wherein the deployable member comprises a petal-shaped wire loop in the deployed configuration.

7. The apparatus of claim 1 wherein the deployable member comprises a plurality of petal-shaped wire loops that at least partially overlap in the deployed configuration.

8. The apparatus of claim 1 wherein the elasticity of the deployable member enables the deployable member to conform to the proximal wall of the bladder without displacing the bladder wall.

9. The apparatus of claim 1 wherein the deployable member is concave with respect to the proximal wall of the bladder in the deployed configuration.

10. The apparatus of claim 1 wherein the plunger further comprises a handle affixed to the proximal end of the plunger.

11. The apparatus of claim 1 wherein the plunger comprises a rigid material.

12. The apparatus of claim 1 wherein the plunger comprises a rigid proximal section and an elastic distal section, the elastic distal section suitable for conforming to the curvature of the catheter.

13. The apparatus of claim 1 wherein the catheter has a length of between 30 cm and 50 cm.

14. Apparatus for facilitating visualization of a patient's prostate/bladder junction, comprising:
a catheter having proximal and distal ends, a proximal deployment port at the proximal end, a first outlet port at the distal end, and a first lumen extending therebetween;
a plunger having proximal and distal ends, the plunger configured to slide longitudinally through the proximal deployment port;
at least one deployable member coupled to the distal end of the plunger, wherein the deployable member is expandable from a delivery configuration adapted for transurethral insertion, to a deployed configuration adapted for engagement of a proximal portion of the patient's bladder; and
a connector having proximal and distal ends, wherein the proximal end of the connector is affixed to the distal end of the plunger, and the distal end of the plunger is affixed to the deployable member.

15. The apparatus of claim 14 wherein the catheter further comprises a second inlet port, a second outlet port and a second lumen extending therebetween.

16. The apparatus of claim 15 wherein the catheter further comprises a third inlet port, a third outlet port and a third lumen extending therebetween.

17. The apparatus of claim 14 wherein the deployable member comprises at least one wire loop.

18. The apparatus of claim 17 wherein the wire loop has a roughened exterior surface, the roughened exterior surface adapted to entrap gas bubbles to facilitate ultrasonic imaging.

19. The apparatus of claim 17 wherein the wire loop comprises a shape memory material.

20. The apparatus of claim 19 wherein the wire loop consists of a Nickel Titanium alloy.

21. The apparatus of claim 14 wherein the deployable member comprises a petal-shape in the deployed configuration.

22. The apparatus of claim 14 wherein the deployable member comprises a plurality of petal-shaped members that at least partially overlap in the deployed configuration.

23. The apparatus of claim 14 wherein the elasticity of the deployable member enables the deployable member to conform to the proximal wall of the bladder without displacing the bladder wall.

24. The apparatus of claim 14 wherein the deployable member is concave with respect to the proximal wall of the bladder in the deployed configuration.

25. The apparatus of claim 14 wherein the plunger further comprises a handle affixed to the proximal end of the plunger.

26. The apparatus of claim 14 wherein the plunger comprises a rigid material.

27. The apparatus of claim 14 wherein the connector is a plastic rod.

28. The apparatus of claim 14 wherein the connector has a coiled configuration.

29. The apparatus of claim 14 wherein the connector has a flexible wire configuration.

30. The apparatus of claim 14 wherein the catheter has a length of between 30 cm and 50 cm.

31. The apparatus of claim 14 further comprising a piece of tubing at least partially covering the deployable member, the tubing suitable for confining gas pockets to enhance ultrasonic imaging around the deployable member.

32. The apparatus of claim 31 further comprising adhesives suitable for affixing the deployable members to the tubing to confine the gas pockets within the tubing.

33. The apparatus of claim 31 wherein a plurality of spaced apart pieces of tubing are spaced along the deployable member.

34. The apparatus of claim 14 wherein the deployable member further comprises a hinging member suitable for rotating the deployable member to a predetermined configuration upon deployment.

35. The apparatus of claim 14 wherein the deployable members comprise a plurality of interwoven wires.

36. Apparatus for facilitating visualization of a patient's prostate/bladder junction, comprising:
a catheter having proximal and distal ends, a proximal deployment port at the proximal end, a first outlet port at the distal end, and a first lumen extending therebetween;
a plunger having proximal and distal ends, the plunger configured to slide longitudinally through the proximal deployment port;
at least one deployable member coupled to the distal end of the plunger, wherein the deployable member is expandable from a delivery configuration adapted for transurethral insertion, to a deployed configuration adapted for engagement of a proximal portion of the patient's bladder; and
a piece of tubing at least partially covering the deployable member, the tubing suitable for confining gas pockets to enhance ultrasonic imaging around the deployable member.

37. The apparatus of claim 36 wherein the catheter further comprises a second inlet port, a second outlet port and a second lumen extending therebetween.

38. The apparatus of claim 37 wherein the catheter further comprises a third inlet port, a third outlet port and a third lumen extending therebetween.

39. The apparatus of claim 36 wherein the deployable member comprises at least one wire loop.

40. The apparatus of claim 39 wherein the wire loop comprises a shape memory material.

41. The apparatus of claim 40 wherein the wire loop consists of a Nickel Titanium alloy.

42. The apparatus of claim 36 wherein the deployable member comprises a petal-shape in the deployed configuration.

43. The apparatus of claim 36 wherein the deployable member comprises a plurality of petal-shaped members that at least partially overlap in the deployed configuration.

44. The apparatus of claim 36 wherein the elasticity of the deployable member enables the deployable member to conform to the proximal wall of the bladder without displacing the bladder wall.

45. The apparatus of claim 36 wherein the deployable member is concave with respect to the proximal wall of the bladder in the deployed configuration.

46. The apparatus of claim 36 wherein the plunger further comprises a handle affixed to the proximal end of the plunger.

47. The apparatus of claim 36 wherein the plunger comprises a rigid material.

48. The apparatus of claim 36 wherein the plunger comprises a rigid proximal section and an elastic distal section, the elastic distal section suitable for conforming to the curvature of the catheter.

49. The apparatus of claim 36 further comprising adhesives suitable for affixing the deployable members to the tubing to confine the gas pockets within the tubing.

50. The apparatus of claim 36 wherein a plurality of spaced apart pieces of tubing are spaced along the deployable member.

51. Apparatus for facilitating visualization of a patient's prostate/bladder junction, comprising:
   a catheter having proximal and distal ends, a proximal deployment port at the proximal end, a first outlet port at the distal end, and a first lumen extending therebetween;
   a plunger having proximal and distal ends, the plunger configured to slide longitudinally through the proximal deployment port; and
   at least one deployable member coupled to the distal end of the plunger, wherein the deployable member is expandable from a delivery configuration adapted for transurethral insertion, to a deployed configuration adapted for engagement of a proximal portion of the patient's bladder,
   wherein the deployable member comprises a hinging member suitable for rotating the deployable member to a predetermined configuration upon deployment.

52. The apparatus of claim 51 wherein the catheter further comprises a second inlet port, a second outlet port and a second lumen extending therebetween.

53. The apparatus of claim 52 wherein the catheter further comprises a third inlet port, a third outlet port and a third lumen extending therebetween.

54. The apparatus of claim 51 wherein the elasticity of the deployable member enables the deployable member to conform to the proximal wall of the bladder without displacing the bladder wall.

55. The apparatus of claim 51 wherein the deployable member is concave with respect to the proximal wall of the bladder in the deployed configuration.

56. The apparatus of claim 51 wherein the plunger further comprises a handle affixed to the proximal end of the plunger.

57. The apparatus of claim 51 wherein the plunger comprises a rigid material.

58. The apparatus of claim 51 wherein the plunger comprises a rigid proximal section and an elastic distal section, the elastic distal section suitable for conforming to the curvature of the catheter.

59. Apparatus for facilitating visualization of a patient's prostate/bladder junction, comprising:
   a catheter having proximal and distal ends, a proximal deployment port at the proximal end, a first outlet port at the distal end, and a first lumen extending therebetween;
   a plunger having proximal and distal ends, the plunger configured to slide longitudinally through the proximal deployment port; and
   at least one deployable member coupled to the distal end of the plunger, wherein the deployable member is expandable from a delivery configuration adapted for transurethral insertion, to a deployed configuration adapted for engagement of a proximal portion of the patient's bladder,
   wherein the deployable member comprises a plurality of interwoven wires.

60. The apparatus of claim 59 wherein the catheter further comprises a second inlet port, a second outlet port and a second lumen extending therebetween.

61. The apparatus of claim 60 wherein the catheter further comprises a third inlet port, a third outlet port and a third lumen extending therebetween.

62. The apparatus of claim 59 wherein the deployable member further comprises at least one wire loop, wherein the plurality of interwoven wires are disposed about the wire loop.

63. The apparatus of claim 62 wherein the wire loop comprises a shape memory material.

64. The apparatus of claim 63 wherein the wire loop consists of a Nickel Titanium alloy.

65. The apparatus of claim 59 wherein the deployable member comprises a petal-shape in the deployed configuration.

66. The apparatus of claim 59 wherein the elasticity of the deployable member enables the deployable member to conform to the proximal wall of the bladder without displacing the bladder wall.

67. The apparatus of claim 59 wherein the deployable member is concave with respect to the proximal wall of the bladder in the deployed configuration.

68. The apparatus of claim 59 wherein the plunger further comprises a handle affixed to the proximal end of the plunger.

69. The apparatus of claim 59 wherein the plunger comprises a rigid material.

70. The apparatus of claim 59 wherein the plunger comprises a rigid proximal section and an elastic distal section, the elastic distal section suitable for conforming to the curvature of the catheter.

71. A method of facilitating visualization of a patient's prostate/bladder junction, the method comprising:
   providing apparatus comprising a catheter having proximal and distal ends, a proximal deployment port at the proximal end, a distal outlet port at the distal end, a first lumen extending therebetween, a plunger having proximal and distal ends, and at least one deployable member affixed to the distal end of the plunger;
   advancing the apparatus through the patient's urethra;
   distally advancing the deployable member beyond the distal outlet port to deploy the deployable member to a predetermined configuration within the patient's bladder;
   proximally retracting the deployable member such that it engages a proximal portion of the patient's bladder; and
   performing brachytherapy on the patient's prostate.

72. The method of claim 71 further comprising injecting an echo-contrast agent to facilitate visualization of the patient's prostate/bladder junction.

73. The method of claim 71 further comprising ultrasonically imaging a junction between the patient's bladder and the patient's prostate.

* * * * *